(12) United States Patent
Peterson

(10) Patent No.: US 6,464,626 B1
(45) Date of Patent: Oct. 15, 2002

(54) CATHETER ASSEMBLY INCORPORATING RADIATION SHIELDING AND RELATED METHOD OF USE

(75) Inventor: Eric Peterson, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/410,491

(22) Filed: Sep. 30, 1999

(51) Int. Cl.[7] .................................................. A61N 5/00
(52) U.S. Cl. ......................................................... 600/3
(58) Field of Search ......................................... 600/1–8

(56) References Cited

U.S. PATENT DOCUMENTS

| | | | |
|---|---|---|---|
| 5,199,939 A | | 4/1993 | Dake et al. ..................... 600/3 |
| 5,213,561 A | * | 5/1993 | Weinstein et al. .............. 600/3 |
| 5,411,466 A | * | 5/1995 | Hess ............................... 600/3 |
| 5,863,284 A | * | 1/1999 | Klein ............................. 600/3 |
| 6,033,357 A | * | 3/2000 | Ciezki et al. .................. 600/3 |
| 6,074,339 A | * | 6/2000 | Gambale et al. ............... 600/3 |

* cited by examiner

Primary Examiner—John P. Lacyk
(74) Attorney, Agent, or Firm—Blakely, Sokoloff, Taylor & Zafman LLP

(57) ABSTRACT

A radioactive catheter system, including a plurality of medical catheter assemblies, to irradiate patient's bodies having a variety of treatment requirements, configured to eliminate the need to maintain a selection of radiation source wires. The catheter assemblies each include a catheter that defines a lumen configured to receive a radiation source wire from an afterloader. Each catheter assembly includes at least one radiation shield configured and located to form a treatment region, so as to shield a portion of the radiation source from irradiating a patient's body. The radiation shield surrounds the lumen circumferentially over a first and second longitudinal portion of the catheter, forming a treatment window configured to only allow portions of the positioned radiation source longitudinally within the treatment window to primarily irradiate portions of the body. The radiation shield may comprise coils of radiation shielding material, or adjacent rings of radiation shielding material. The catheter assembly may include radial centering devices adjacent the radiation shield. The plurality of catheter assemblies include a plurality of different treatment regions to accommodate a variety of treatment requirements.

23 Claims, 5 Drawing Sheets

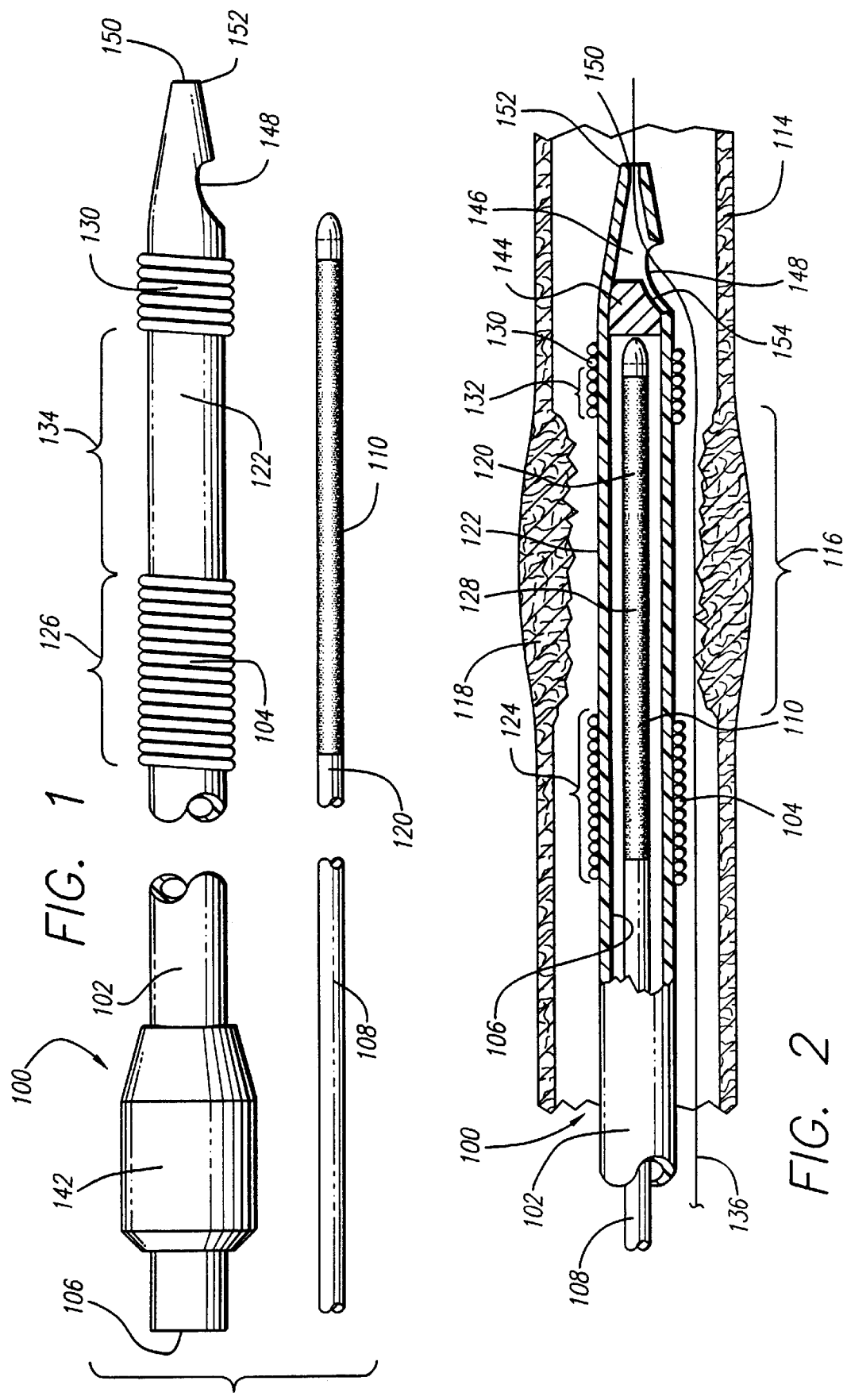

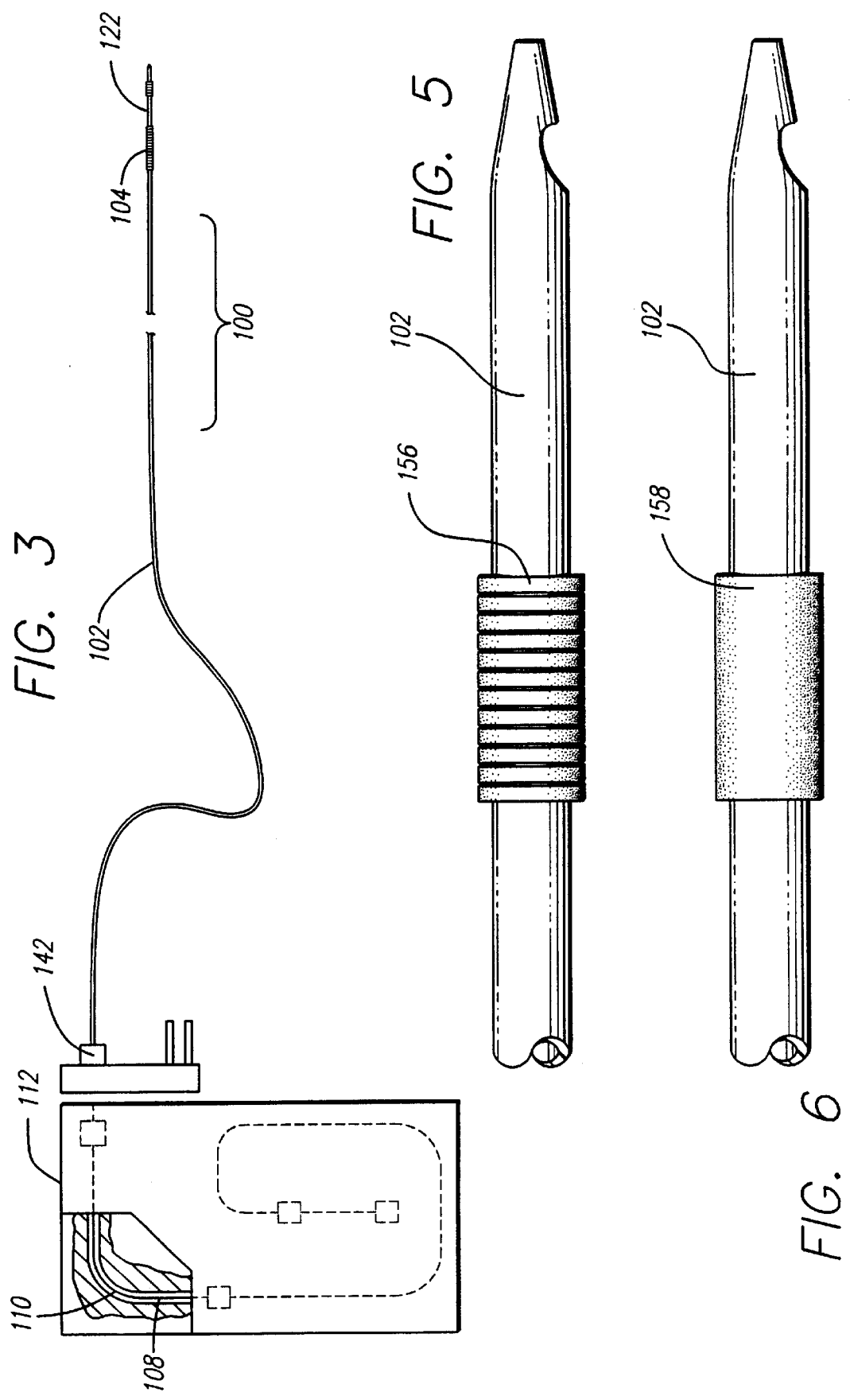

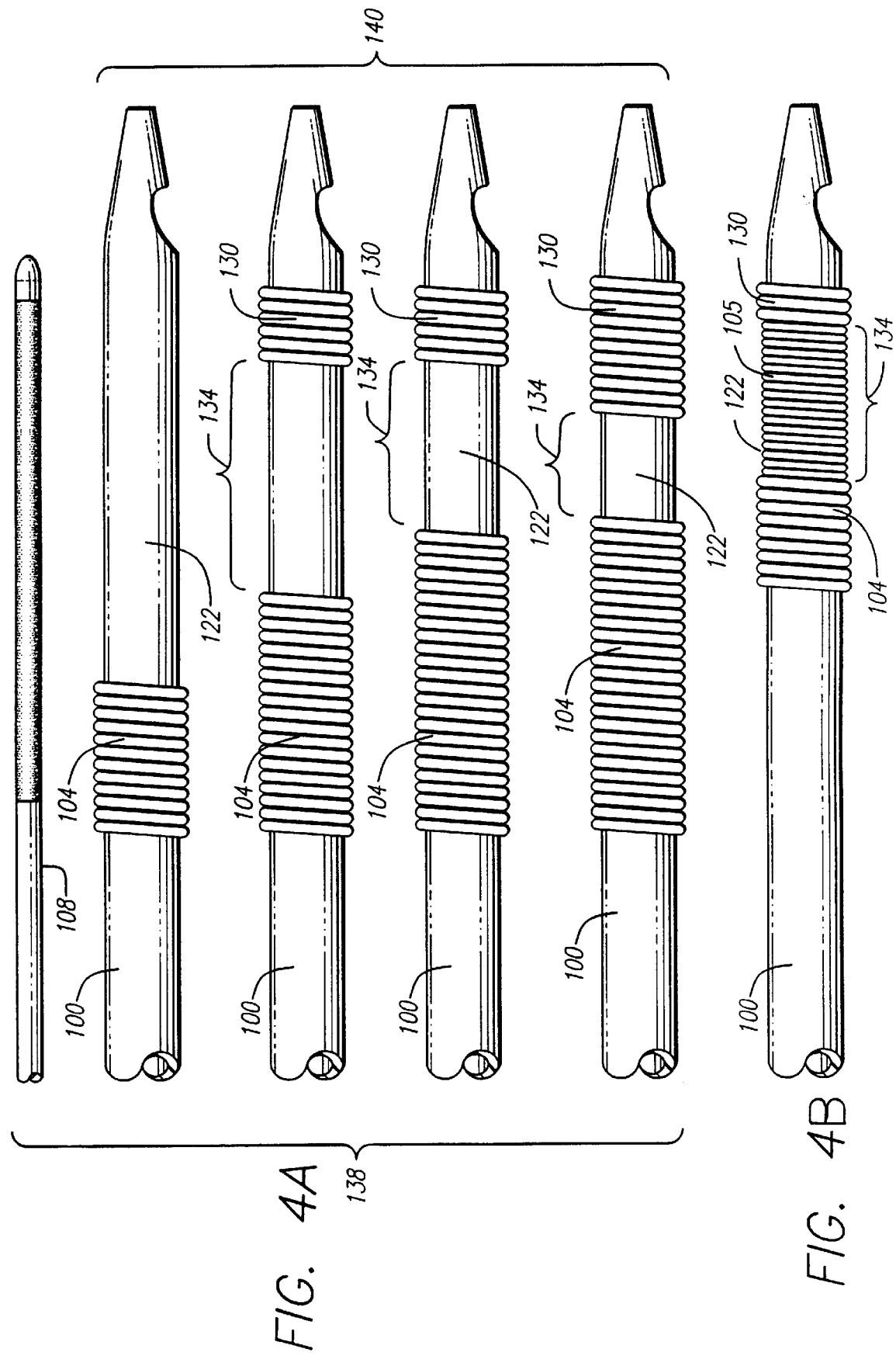

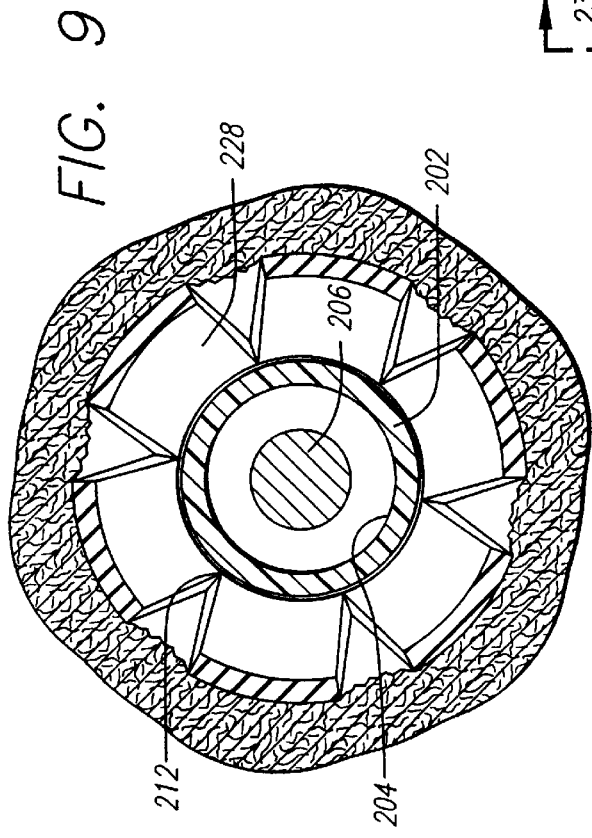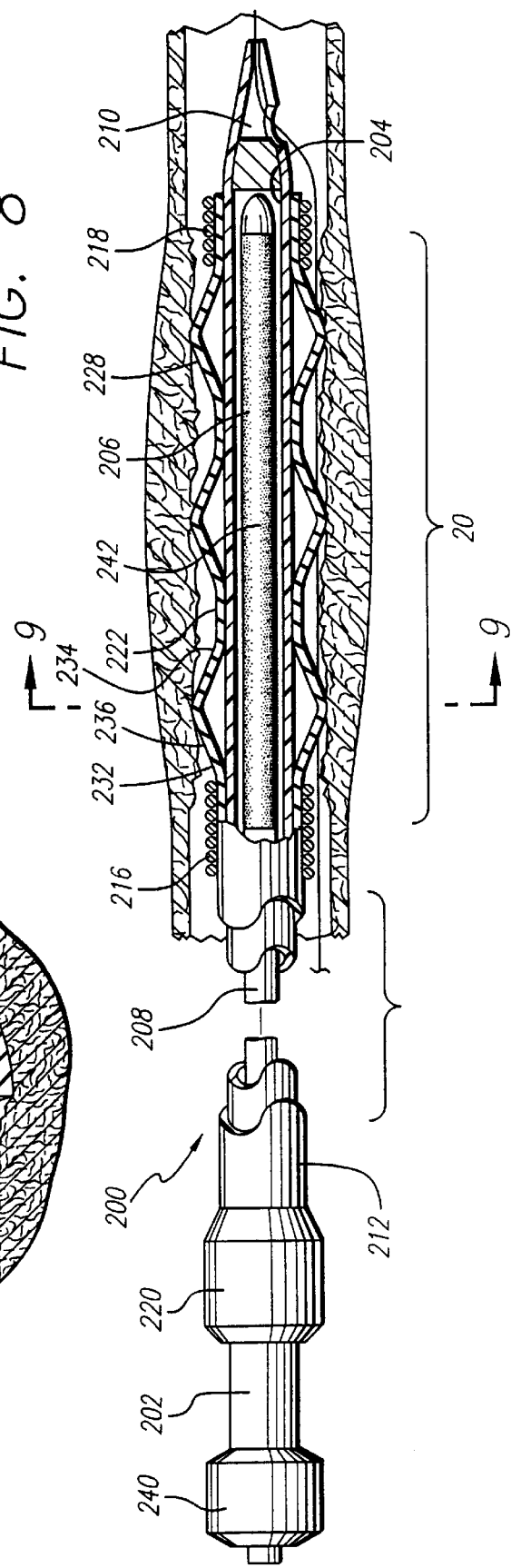

CATHETER ASSEMBLY INCORPORATING RADIATION SHIELDING AND RELATED METHOD OF USE

FIELD OF THE INVENTION

This invention relates generally to catheter-type apparatus for use in treating a patient and, more particularly, to a radiation treatment system including a radioguide catheter having radiation shielding and a related method of use.

BACKGROUND OF THE INVENTION

Physicians now use radiation to treat an increasing number of medical problems. One form of radiation treatment involves the insertion of a radioactive source wire, carrying a radiation source, into a patient's body. The radiation source incorporates a radioactive isotope. Typically, a physician feeds the source wire into the patient's body through a lumen of an implanted radioguide catheter.

Because different patients require a variety of different radiation treatments, a physician presently needs the availability of a wide selection of radioactive source wires. This selection may include radiation sources having both different lengths and different levels of radioactivity. Furthermore, because radioactive isotopes have limited half-lives, the radiation sources have a limited usage life. Thus, this selection of radioactive source wires, and their radiation sources, needs replacement on a regular basis, at significant expense.

One use of such a radioactive source wire is intravascular radiotherapy (IRT). IRT prevents or controls restenosis following percutaneous transluminal angioplasty (PTA), as described in U.S. Pat. No. 5,199,939. IRT also shows promise in the prevention or long-term control of stenosis following a cardiovascular graft procedure or other trauma to a vessel wall.

A physician performing PTA typically examines an area of a blood vessel suffering from stenosis, and then selects a balloon catheter having a length and diameter commensurate with the length and diameter of the stenosis. The physician threads a guide wire and a guide catheter to the area of stenosis, and then uses the guide wire and guide catheter to guide the balloon catheter to its desired position. Actuated by the physician, the balloon catheter expands the area of stenosis. Finally, the physician removes the balloon catheter, leaving the guide wire and guide catheter in place if another procedure, such as IRT, is to follow.

To perform IRT, the physician selects a radioactive source wire that carries a radiation source commensurate in length and diameter to the expanded area of stenosis. The source wire typically takes the form of a solid nickel-titanium alloy core, and the radiation source takes the form of a radioactive isotope, such as iridium, or Phosphorus-32 embedded within the source wire, at its distal tip. This radiation source must be used with extreme care. Even short exposures at close distances can result in radiation injury.

The source wire is initially stored in a remote afterloader, which includes a heavily shielded storage compartment for shielding the radiation source when the source wire is fully retracted into the afterloader. Changing the source wire is a difficult process, entailing risks of radiation exposure.

The IRT is performed by advancing a flexible, radioguide catheter through the implanted guide catheter and along the implanted guide wire in a patient's cardiovascular system until the radioguide catheter's distal end is at or near the vessel region to be treated, e.g., the region previously subjected to the angioplasty procedure. Preferably, the radioguide catheter is radially centered in the vessel region.

After the radioguide catheter has been positioned, the afterloader advances the source wire longitudinally through a lumen of the radioguide catheter until the source wire's radiation source reaches the vessel region to be treated. The radiation source is held in this region for a prescribed time duration, calculated to deliver an effective dosage of radiation. After irradiating the region, the source wire is withdrawn back into the afterloader.

The length of the patient's stenosis to be treated can vary widely, and thus a physician generally must have access to a wide selection of source wires and radiation sources to treat any length stenosis. As was more generally discussed above, maintaining such a selection can be quite expensive.

The required selection of source wires can be limited by simulating a radiation source of a preferred length using a radiation source of much shorter length. In particular, a relatively short radiation source can be sequentially positioned at a plurality of locations along the treatment location in the patient's body, to simulate a preferred length. This treatment method, however, can require a substantially longer period of time to complete. In particular, the radiation source must be positioned at each of a plurality of locations for roughly the same period of time that the preferred-length radiation source would be positioned at a single location in the body. This increased duration can cause both additional expense in general intervention costs, and additional risk of harm due to prolonged vessel obstruction.

In addition to length, arteries to be treated vary greatly in diameter, with typical values ranging from 2.0 mm to 4.0 mm. Since the radiation delivered by IRT sources drops rapidly with distance from the source, this variation in diameter causes the dose rate in a 2.0 mm diameter artery to be much higher than the dose rate for the same source treating a 4.0 mm diameter artery. This wide variation in dose rate has the potential to impact the efficacy of the IRT therapy.

Moreover, the dose rate must be controlled so as not to exceed safe levels of radiation delivered to the patient. There could be a negative effect if the dose rate is too high for a particular vessel region.

It should therefore be appreciated that a definite need has existed for a device to irradiate patients having a variety of treatment requirements, without requiring the expense of maintaining a selection of radioactive source wires having radiation sources of different lengths and activities, and without requiring the risks involved in frequently changing from one source wire to another. The present invention satisfies these and other needs, and provides further related advantages.

SUMMARY OF THE INVENTION

The present invention provides a medical catheter assembly and a related method of using the catheter assembly. A catheter assembly of the invention modifies the effective radioactive configuration of a radiation source when the radiation source is positioned within a patient's body. The catheter assembly includes a catheter to be inserted into the patient's body. The catheter defines a lumen configured to receive and position the radiation source within the patient's body.

A catheter assembly of the invention includes a means for modifying the effective radioactive configuration of the positioned radiation source. The modifying means defines a treatment region. More particularly, this modifying means may be a radiation shield shielding a portion of the lumen. The radiation shield is configured and located to define the treatment region, modifying the effective radioactive configuration of the radiation source when it is positioned within the patient's body.

A method of irradiating a portion of a patient's body with a radiation source includes inserting a medical catheter assembly into the patient's body. The catheter assembly includes a catheter defining a lumen and a radiation shield. The method can also include positioning the radiation source into the catheter's lumen such that the radiation shield shields a portion of the body from the positioned radiation source.

Other features and advantages of the invention will become apparent from the following detailed description, taken in conjunction with the accompanying drawings, which illustrates, by way of example, the principals of the invention.

BRIEF DESCRIPTION OF THE DRAWINGS

FIG. 1 is an elevational view of an embodiment of a medical catheter assembly embodying features of the present invention.

FIG. 2 is a cross-sectional elevational view of a distal end of the medical catheter assembly depicted in FIG. 1, positioned on a guide wire within a vessel suffering from stenosis, after percutaneous transluminal angioplasty (PTA).

FIG. 3 is an elevational view of the medical catheter assembly depicted in FIG. 1, attached to an afterloader.

FIG. 4A is an elevational view of a radiation treatment system embodying features of the present invention.

FIG. 4B is an elevational view of another embodiment of a medical catheter assembly embodying features of the present invention.

FIG. 5 is a partial elevational view of yet another embodiment of a medical catheter assembly embodying features of the present invention.

FIG. 6 is a partial elevational view of yet another embodiment of a medical catheter assembly embodying features of the present invention.

FIG. 8 is an elevational cut-away view of the medical catheter assembly depicted in FIG. 7, positioned on a guide wire within a vessel suffering from stenosis, after PTA, with radial supports extended.

FIG. 9 is a cross-sectional end view of the medical catheter assembly depicted in FIG. 8, taken along line 9—9 of FIG. 8.

DETAILED DESCRIPTION OF THE PREFERRED EMBODIMENTS

Figure 7:
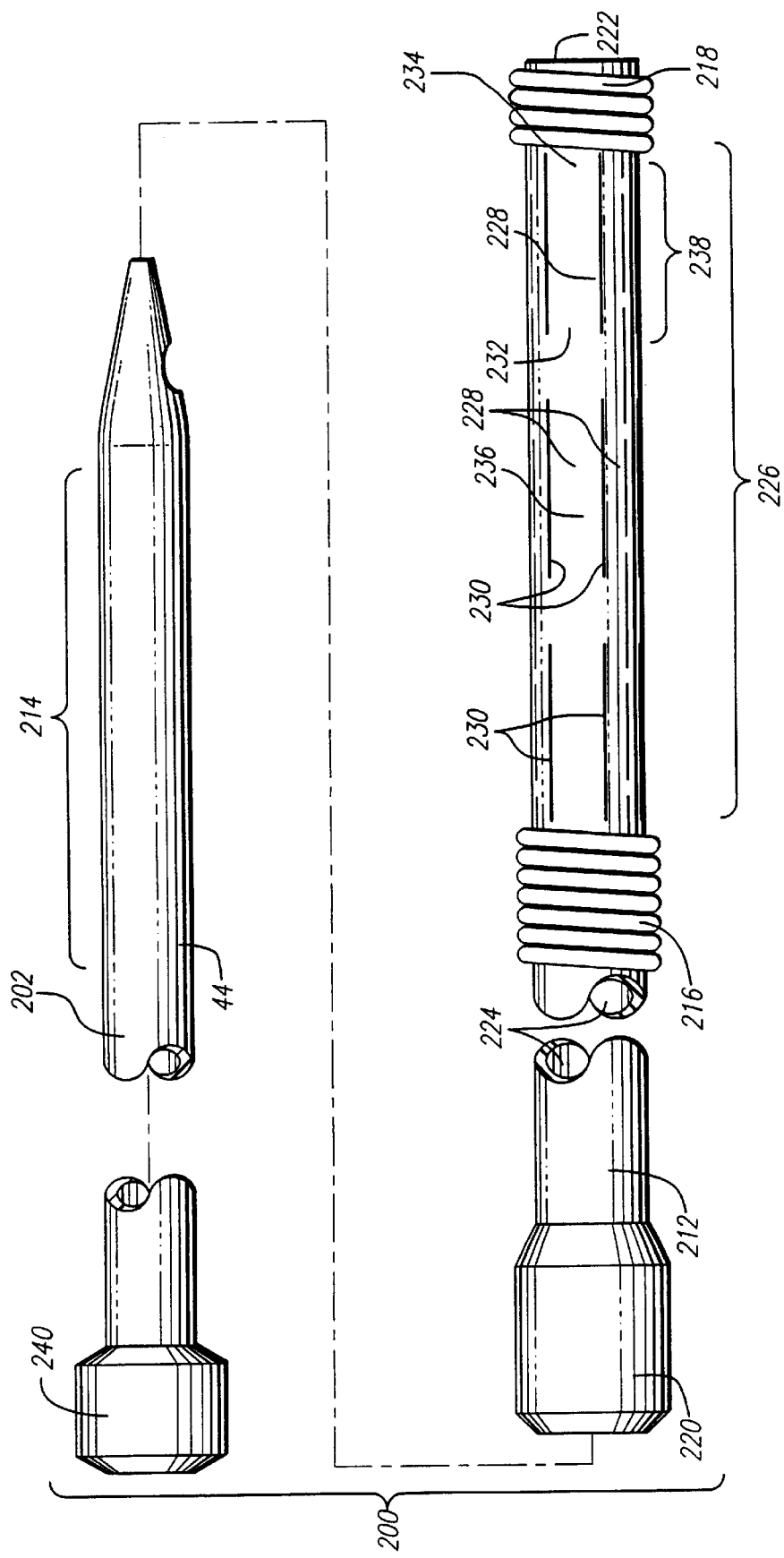
FIG. 7 is an exploded view of yet another embodiment of a medical catheter assembly embodying features of the present invention.

The present invention is embodied in a medical catheter assembly, a related method of using the catheter assembly, and a related radiation treatment system, for use within a patient's body. The catheter assembly is suitable for modifying the effective radioactive configuration of a radiation source positioned within the catheter assembly while inserted within a patient's body. The modified, effective radioactive configuration of the positioned and inserted radiation source principally irradiates a predetermined portion of the patient's body. Embodiments of the present invention offer advantageous use in both human and veterinary medicine.

The catheter assembly of the present invention includes a treatment region giving a physician the ability to primarily irradiate a precise portion of the patient's body. This irradiation may be applied with a radiation source that is not itself of a desired radioactive configuration. Advantageously, this allows the physician, or a related institution providing equipment to the physician, to maintain either one or a limited number of radiation sources. Such radiation sources are expensive and have a short usable lifetime, and thus these features may provide for significant cost savings.

The present invention can improve safety and reduce setup time in preparing for the patient's irradiation. In particular, the radiation sources are often highly radioactive, and thus require numerous safety precautions to handle. For use, the radiation sources generally must be placed in a container providing shielded storage and automated use. Changing the container's radiation source takes time and expense, and entails a risk of dangerous exposure to radiation. The number of these radiation source changes is minimized by limiting the number of radiation sources to be used.

The catheter assembly includes at least one radiation shield. Preferably, two radiation shields are provided that form a treatment window. The treatment window allows precise control over the portion of the body to be irradiated, even where there is not precise control over the location of the radiation source within the lumen. In particular, when the radiation shields forming the treatment window extend over a distance substantially longer than the radiation source's length, then the radiation source may be positioned at any of a large variety of positions and still radiate effectively through the entire treatment window.

The radiation shield may either comprise a coil of radiation shielding material, or adjacent rings of radiation shielding material. The coil, or set of adjacent rings, may be located around the catheter, providing a radiation shield that surrounds the lumen circumferentially along a portion of the catheter. Such a configuration allows for the necessary flexibility to move the catheter along tortuous blood vessels or other body lumens, while providing radiation shielding that shields portions of the radiation source from primarily irradiating the body.

The radiation shields may provide positional guidance for a physician using X-ray technology to monitor the positioning of the catheter. Thus, the catheter assembly does not need to include separate markers for X-ray positional guidance.

The radiation shield may further include a centering device, where the radiation shield is adjacent to the centering device. This is particularly useful when the radiation source needs to be centered in the patient's vessel in order to equalize irradiation of the vessel circumferentially around the radiation source. By locating the radiation shield adjacent to the centering device, the risk of irradiation occurring from a non-centered portion of the catheter is small.

A plurality of catheter assemblies, featuring some or all of the above features, may be combined in a set as a radiation treatment system. The system may include a plurality of different treatment regions. This system advantageously provides a single radiation source, or a limited number of radiation sources, with the capability to be used on patients with a variety of treatment requirements.

The catheter assembly includes radiation shields mounted on a radioguide catheter, the radiation shields being at least substantially opaque to the radiation source's radiation over at least a portion of the shields. The radiation shields substantially prevent the positioned and inserted radiation source from irradiating the patient's body through other than a treatment region of the catheter assembly. The treatment region is thus defined as an area of the catheter assembly that is principally transparent or translucent to radiation from the radiation source when the radiation source is positioned within the radioguide catheter. The positioned and inserted radiation source thus principally irradiates the predetermined portion of the patient's body.

The catheter assembly of the present invention provides physicians with the ability to irradiate patients having a variety of treatment requirements, without the expense of maintaining a selection of radiation source wires, and without the risk of exposure involved in frequently changing source wires. For a given source wire, an associated catheter assembly includes one or more radiation shields located and configured to form a desired treatment region. A plurality of catheter assemblies, each having a different treatment region, thus allow a single radiation source wire to meet a variety of treatment requirements.

The present invention can be used for intravascular radiotherapy (IRT). During IRT, a blood vessel is exposed to a radiation source. Such exposure helps prevent restenosis after percutaneous transluminal angioplasty (PTA), or other invasive procedures such as a stent insertion, an atherectomy, or laser angioplasty. The radiation treatment of cancerous tissue in the body is another use for embodiments of the invention.

With reference to FIGS. 1–3, a medical catheter assembly 100 for use in IRT, according to the present invention, includes a radioguide catheter 102 and a first radiation shield 104. The radioguide catheter defines a lumen 106 to receive a source wire 108 carrying a radiation source 110 at its distal end 120.

As shown in FIG. 2, the medical catheter assembly 100 is configured to be inserted within a blood vessel 114, which includes a portion 116 to be treated. This portion to be treated is an area of stenosis 118 previously expanded in a PTA procedure, as well as a portion of the surrounding tissue which is at risk of restenosis. A distal end 120 of the source wire 108 carries the radiation source 110 to be used to irradiate the portion of the vessel to be treated.

The first radiation shield 104 extends longitudinally along a portion of a distal end of the radioguide catheter 102, defining a treatment region 122 of the catheter assembly. The first radiation shield is configured and located to shield a first portion 124 of the radiation source 1 10 from primarily irradiating the patient's body when the radiation source is positioned within the patient's body, in the inserted catheter's lumen. In particular, the first radiation shield is configured to surround the lumen circumferentially over a first longitudinal portion 126 of the lumen, shielding that portion of the lumen and surrounding the positioned radiation source up to a longitudinal, exposed section 128 in the catheter assembly's treatment region. The first radiation shield is preferably configured as a coil wrapped around the radioguide catheter, and thus is flexible enough to bend around tortuous vessel passages. A radio-opaque material, such as gold or tungsten, is used in making the first radiation shield.

As shown in FIG. 4A, the catheter assembly 100 includes a second radiation shield 130, further defining the treatment region 122. The second radiation shield is configured and located to shield a second portion 132 of the radiation source 110 from primarily irradiating the patient's body when the radiation source is positioned within the patient's body, in the inserted catheter's lumen.

In one embodiment, the first and second radiation shields surround the lumen circumferentially over first and second longitudinal portions of the catheter, forming a treatment window configured to only allow portions of the positioned radiation source longitudinally within the treatment window to primarily irradiate portions of the body. The second radiation shield may be integral with the catheter.

The first radiation shield 104 and second radiation shield combine to form a treatment region that is a treatment window 134, to better control the size of the radiation source's exposed section 128. The treatment window is configured to only allow portions of the positioned radiation source longitudinally within the treatment window to primarily irradiate portions of the body. Similar to the first radiation shield, the second radiation shield is preferably configured as a coil wrapping around the radioguide catheter 102 and is spaced apart from the first radiation shield.

As shown in FIG. 4B, a third radiation shield 105, designed to reduce the delivered radiation dose by a selected percentage, can be configured between the first and second shields 104 and 130 to reduce the effective dose rate of the radiation source 110 (shown in FIG. 4A). The highest level of attenuation would be employed on catheters designed for small arteries, while no third shield 105 would be employed on catheters designed for larger arteries. Preferably, the third shield 105 reduces the delivered radiation dose by 20 to 80%. The result of this variable attenuation will be a set of catheters which deliver a relatively uniform dose rate to the artery wall across a wide range of artery diameters, using a single source.

The third radiation shield 105 can be configured as a coil wrapped around the radioguide catheter 102. The third radiation shield 105 is preferably located between first radiation shield 104 and second radiation shield 130. Third radiation shield 105 covers treatment region 122 of the catheter assembly 100. In the example of the catheter assembly 100 shown in FIG. 4B, third radiation shield 105 extends over the entire length of the treatment window 134. Also, as shown in FIG. 4B, first radiation shield 104 can have a shorter longitudinal length.

Third radiation shield 105 has a coil configuration similar to that of radiation shields 104 and 130. Other configurations of third radiation shield 105 can be provided, in a similar manner as previously described with respect to radiation shields 104 and 130. Third radiation shield 105, however, has a different thickness than radiation shields 104 and 130. In the example shown in FIG. 4B, third radiation shield 105 is formed of a coil having a smaller wire diameter than of first and second radiation shields 104 and 130. Thus, third radiation shield 105 is not as opaque to the radiation source's radiation as the thicker shields 104 and 130.

With reference to FIGS. 1–4, a physician typically begins a PTA by inserting a guide wire 136 into a blood vessel (not shown) in the patient's groin area. Using X-ray projection (not shown) to guide the work, the physician advances the guide wire up through the vascular system (not shown) until it reaches the region of the coronary vessel 114 suffering from stenosis. A guide catheter, having a lumen, can be guided up the guide wire to serve to guide other catheters through the patient. A PTA balloon catheter (not shown) is selected based on the length of the stenosis. The balloon catheter is threaded onto and guided up the guide wire, and through the guide catheter, until the balloon is positioned within the stenosis. The physician inflates the balloon, expanding the artery in the area of the stenosis. The physician then completes the PTA by deflating the balloon and removing the PTA balloon catheter, while leaving the guide wire and guide catheter in place.

Continuing with an IRT, the physician uses a radiation treatment system 138 comprising a source wire 108 and a set 140 of catheter assemblies 100 configured to be used with the source wire. The set of catheter assemblies are configured with a plurality of different radiation shields 104 and 130 located and configured to form a plurality of different treatment regions 122. Preferably, these treatment regions are treatment windows 134 of different lengths.

The physician begins the IRT by selecting a catheter assembly configured such that the radiation shields 104 and 130 form a treatment region 122 that is suitable to allow the preferred length of radiation source exposed section 128 when used with the source wire. Preferably, the physician selects a catheter assembly suitable for windowing the source wire to better control the effective size of the radiation source's exposed section. The physician then threads the catheter assembly along the guide wire 136 and through the guide catheter (not shown). The catheter assembly's treatment region is positioned within the now-expanded area of stenosis 118, which is the longitudinal portion 116 of the vessel 114 to be treated. More particularly, the radioguide catheter's distal end is positioned such that its unshielded portion will provide radiation to the portion of the artery affected by the PTA. Preferably, the catheter assembly 100 is configured to radially center the source wire's radiation source 110 in the vessel's portion 116 to be treated, such as with a balloon, or other mechanical centering device (not shown).

Referring to FIG. 3, the physician connects a proximal end 142 of the catheter assembly to the afterloader 112 containing the source wire 108. As shown in FIG. 2, the afterloader rapidly threads the source wire up through the radioguide catheter's lumen 106, positioning the radiation source such that it is shielded, except for an exposed portion that radiates through the treatment region 122 (thus irradiating the expanded area of stenosis 118). Thus, the catheter assembly effectively modifies the radioactive configuration of the radiation source. When a desired level of radiation exposure is reached, the afterloader rapidly retracts the source wire from the radioguide catheter 102. The catheter assembly and guide wire 136 may then be carefully removed from the patient's vessel 114.

Turning now to the structural details of the catheter assembly 100, and with reference to FIGS. 1–2, the catheters lumen 106 extends from the catheter's proximal end 142 to the treatment region 122, forming a passage to carry the source wire 108. Preferably the catheter's lumen is closed, and includes a plug 144 distal to the treatment region. The plug seals the lumen so that the lumen may only be accessed from the proximal end of the radioguide catheter 102. The sealed lumen allows a non-sterile source wire to be positioned within a patient's body without contaminating the patient. Furthermore, the plug serves to limit the longitudinal position of the source wire in the lumen, and thus better assure that the radiation source 110 is properly positioned with respect to the radiation shields 104 and 130.

The radioguide catheter 102 may include X-ray markers (not shown) to demarcate the treatment region 122 of the catheter. These markers provide positional guidance to the physician when using the catheter assembly 100 in conjunction with X-ray viewing. Preferably, however, radiation shields are used for positional guidance, and the radioguide catheter contains no separate markers for positional guidance.

The radioguide catheter 102 preferably defines a second passage 146, for receiving the guide wire 136 so that the radioguide catheter may be advanced over the guide wire. Most preferably, this guide wire passage extends from a first opening 148 at the distal end of the radioguide catheter to a second opening 150 at the tip 152 of the radioguide catheter's distal end. However, the guide wire passage may have other configurations, such as one extending through the full length of the radioguide catheter in parallel with the source wire lumen. Preferably, the plug 144 is adjacent the guide wire passage's first opening, and forms a ramp 154 to direct the guide wire through the guide wire passage.

The radiation shields' coil configuration, as shown in this first embodiment of the invention, is flexible. The radiation shields are preferably flexible to allow the catheter assembly to be threaded through tortuous vessels. With reference to FIG. 5, a second preferred embodiment of the invention, which is also flexible, includes a radiation shield configured as a series of solid rings 156 surrounding the radioguide catheter 102. These solid rings are integral with the radioguide catheter. A third embodiment of the invention includes a radiation shield configured as a solid tube 158, as depicted in FIG. 6. Other embodiments may use longitudinal variations of the radioguide catheter's material properties, such as by variation of material type or thickness, to form radiation shields. For example, the radioguide catheter may be made from radiation shielding material, except for a treatment region made from a material that is transparent to radiation.

Depicted in FIGS. 7–9, a fourth, and preferred embodiment of the present invention is also for use in intravascular radiotherapy (IRT). This catheter assembly 200 includes a radioguide catheter 202 similar in design to that of the first embodiment, i.e., it is configured with a lumen 204 to receive a radiation source 206 on a source wire 208, and a guide wire passage 210. The fourth embodiment also includes a sleeve 212 for centering a treatment region 214 of the catheter assembly. Two radiation shields 216 and 218, located on the sleeve, are configured to form the treatment region when the catheter assembly is inserted into the patient's body and the treatment region is centered in the vessel.

The sleeve 212 is a tubular catheter; however, it will be referred to as a sleeve in this Detailed Description for the sake of clarity. The sleeve extends longitudinally from a proximal end 220 to a distal end 222. Thus, the sleeve forms a lumen 224, which contains substantially the full length of the radioguide catheter 202, with only a small portion at each end of the radioguide catheter protruding from either end of the sleeve. The sleeve's distal end connects to the radioguide catheter's distal end. The portion of the radioguide catheter's distal end containing the guide wire passage 210 extends beyond the distal end of the sleeve.

A portion 226 of the sleeve 212, longitudinally proximate to the treatment region 214, includes extendable radial supports 228 situated to center the treatment region. The sleeve is configured to center the catheter assembly's treatment region within the vessel, along with the positioned radiation source, and thus the sleeve is suitable to provide catheter radial positioning such that the vessel's portion to be treated is treated with equal radiation exposure around its circumference. The radial supports thus form a centering device for the catheter assembly.

The radial supports 228 are formed by a plurality of slits 230 on the sleeve. Preferably, the radial supports comprise longitudinally running strips having two ends 232 and 234. Each radial support extends when its ends are moved with respect to each other. Specifically, this movement buckles, or bends, the radial support, causing a central portion 236 of the radial support to move radially outward. The outward-moving central portion contacts the vessel, to partially restrict the radial position of the sleeve within the vessel. Reversing the relative movement of the radial support's ends causes the radial support to retract.

The sleeve 212 is configured with a set 238 of radial supports 228 positioned around its full circumference at a given longitudinal location. The sleeve preferably includes more than one set of radial supports. The radial supports are extended and retracted by relatively moving the proximal end 220 of the sleeve and a proximal end 240 of the radioguide catheter 202.

The radiation shields 216 and 218 extend longitudinally along portions of the sleeve 212, adjacent to the longitudinal portion 226 having radial supports 228. The radiation shields are configured to shield the patient's body from principally being irradiated by the positioned radiation source 206, other than from the treatment region of the catheter assembly. In particular, the radiation shields are configured to surround the radiation source circumferentially, except for an exposed section 242 of the radiation source in the treatment region.

Because the radiation shields 216 and 218 extend longitudinally along the sleeve 212 adjacent to the portion 226 having radial supports 228, this embodiment provides for an exposed section 242 of the radiation source 206 that is assured to be centered. Radiation shields placed adjacent a centering balloon on a radioguide catheter would also embody this feature.

While the preferred catheter assemblies include one or two radiation shields that shield around the circumference of the lumen to form a treatment window, other treatment regions are within the scope of the invention. For instance, a radiation shield providing a treatment window around only a portion of the circumference of the catheter assembly is suitable to provide radiation treatments that are circumferentially aimable. This treatment region usefully provides radiation to a body portion adjacent to a body cavity containing the catheter assembly, rather than to provide radiation circumferentially around the cavity.

Likewise, the radiation shield could be configured to partially shield portions of the body from radiation, i.e., be translucent to radiation. Such shielding could effectively be provided by an intermittent shield, such as a helical shield having space between its coils, or by a variation in shielding material or thickness. Using such a device, a high level radiation source could be used to provide lower levels of radiation, or a single source could provide high level radiation to one body portion and low level radiation to another body portion.

Similarly, while a source wire carrying a radiation source is the typical and preferred means of providing the radiation source to the body, other means of delivering radiation sources within a catheter lumen may be used. Catheter assemblies configured for these radiation sources are well within the scope of the invention. This could be useful for providing reduced dosages to the smaller, distal portions of coronary vessels that vary in size rapidly over the treated area. This could also be used to provide circumferential control over the direction of the radiation treatment.

Thus, the scope of the invention encompasses a wide array of catheter assemblies including a wide array of radiation shields to shield portions of a radiation source from irradiating a patient's body. From the foregoing description, it will be appreciated that the present invention provides a medical catheter assembly to irradiate patients having a variety of treatment requirements, without requiring the expense of maintaining a multitude of radiation source wires or the risks involved in changing from one source wire to another. The present invention also provides for a related radioactive catheter system, and a related method of using the catheter assemblies.

While a particular form of the invention has been illustrated and described, it will be apparent that various modifications can be made without departing from the spirit and scope of the invention. Thus, although the invention has been described in detail with reference only to the preferred embodiments, those having ordinary skill in the art will appreciate that various modifications can be made without departing from the invention. Accordingly, the invention is not intended to be limited, and is defined with reference to the following claims.

I claim:

1. A medical catheter assembly comprising:
   a radioguide catheter comprising an elongated shaft defining a radiation source wire lumen therethrough; and
   a first radiation shield, being substantially opaque to radiation over at least a portion of the first radiation shield, the radiation shield mounted on the shaft and surrounding the shaft of the radioguide catheter to define a treatment region that is principally transparent or translucent to radiation.

2. The medical catheter assembly of claim 1 further comprising a second radiation shield configured and located on said catheter to further define the treatment region.

3. The medical catheter assembly of claim 2 wherein said first radiation shield surrounds said lumen circumferentially over a first longitudinal portion of said catheter, and said second radiation shield surrounds said lumen circumferentially over a second longitudinal portion of said catheter, forming a treatment region that is a treatment window.

4. The medical catheter assembly of claim 1 wherein said catheter's lumen is configured to receive a radiation source carried on a source wire.

5. The medical catheter assembly of claim 1 wherein said first radiation shield is integral with said catheter.

6. The medical catheter assembly of claim 1 wherein said first radiation shield comprises a coil of radiation shielding material.

7. The medical catheter assembly of claim 1 wherein said first radiation shield comprises adjacent rings of radiation shielding materials.

8. The medical catheter assembly of claim 1 wherein said first radiation shield comprises a band of radiation shielding material.

9. The medical catheter assembly of claim 1 wherein the catheter assembly includes markers for X-ray positional guidance.

10. The medical catheter assembly of claim 1 further comprising a centering device, wherein said first radiation shield is adjacent to said centering device.

11. A radiation treatment kit comprising:
    a plurality of catheter assemblies, each catheter assembly including
      a catheter defining a lumen, and
      a first radiation shield, being substantially opaque to radiation over at least a portion of said first radiation shield, the first radiation shield located on the catheter to define a treatment region that is principally transparent or translucent to radiation;

wherein said plurality of catheter assemblies are configured with a plurality of different treatment regions.

12. The radiation treatment kit of claim 11 further comprising a radiation source wire carrying a radiation source.

13. The radiation treatment kit of claim 11 wherein at least one catheter assembly further includes a second radiation shield configured and located on said catheter to further define the catheter assembly's treatment region.

14. The radiation treatment kit of claim 13 wherein:
for each catheter assembly, said first radiation shield surrounds the lumen circumferentially over a first longitudinal portion of said catheter, and said second radiation shield surrounds the lumen circumferentially over a second longitudinal portion of said catheter, the first and second radiation shields defining the region between the first and second longitudinal portions; and
said plurality of catheter assemblies are configured with a plurality of different treatment region lengths.

15. The radiation treatment kit of claim 11 wherein each catheter's lumen is configured to receive a radiation source carried on a source wire.

16. The radiation treatment kit of claim 11 wherein for each catheter assembly, said first radiation shield comprises a coil of radiation shielding material.

17. The radiation treatment kit of claim 11 wherein for each catheter assembly, said first radiation shield comprises adjacent rings of radiation shielding material.

18. The radiation treatment kit of claim 11 wherein for each catheter assembly, said first radiation shield comprises a band of radiation shielding material.

19. The radiation treatment kit of claim 11 wherein for each catheter assembly, said catheter assembly includes markers for X-ray positional guidance.

20. The radiation treatment kit of claim 11 wherein for each catheter assembly, said catheter assembly further comprises a centering device, and said first radiation shield is adjacent to the centering device.

21. A method for irradiating an area of stenosis in a patient's body with a radiation source, the method comprising:
inserting a medical catheter assembly into a patient's body, said catheter assembly including a radioguide catheter defining a radiation source wire lumen and further including a radiation shield that defines a treatment region by shielding a portion of said lumen;
positioning the radiation shield such that the treatment region is positioned within the area of stenosis in the patient's body;
threading a radiation source wire having a radiation source at an end of said wire through said lumen; and
positioning the radiation source such that it is shielded by the radiation shield except for an exposed portion that irradiates the area of stenosis through the treatment region.

22. A method for modifying the effective radioactive configuration of a radiation source, comprising:
positioning a catheter assembly within a patient's body, the catheter assembly defining a radiation source wire lumen, the catheter assembly including a radiation shield;
threading a radiation source wire having a radiation source at an end through the catheter's lumen; and
positioning the radiation source within the radiation shield such that the effective radioactive configuration of the radiation source is modified.

23. The method of claim 22, wherein said radiation shield is substantially opaque to the radiation source's radiation over at lease a portion of said radiation shield.

* * * * *

UNITED STATES PATENT AND TRADEMARK OFFICE
CERTIFICATE OF CORRECTION

PATENT NO.     : 6,464,626 B1
DATED          : October 15, 2002
INVENTOR(S)    : Peterson It is certified that error appears in the above-identified patent and that said Letters Patent is hereby corrected as shown below:

Column 12,
Line 33, please delete "lease" and insert -- least --.

Signed and Sealed this

Ninth Day of September, 2003

JAMES E. ROGAN
*Director of the United States Patent and Trademark Office*